United States Patent
Schneider (10) Patent No.: US 8,882,648 B2
(45) Date of Patent: Nov. 11, 2014

(54) METHOD AND APPARATUS FOR ASSEMBLING AND FOLDING ABSORBENT ARTICLES

(75) Inventor: Uwe Schneider, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 510 days.

(21) Appl. No.: 13/311,982

(22) Filed: Dec. 6, 2011

(65) Prior Publication Data
US 2012/0157280 A1 Jun. 21, 2012

Related U.S. Application Data

(60) Provisional application No. 61/424,720, filed on Dec. 20, 2010.

(51) Int. Cl.
*A61F 13/49* (2006.01)
*A61F 13/15* (2006.01)

(52) U.S. Cl.
CPC ..... *A61F 13/15747* (2013.01); *A61F 13/15764* (2013.01)
USPC ............ 493/374; 493/379; 493/382; 493/388

(58) Field of Classification Search
CPC .............. A61F 13/49; A61F 13/15747; A61F 13/15585; A61F 13/15756; B65H 2406/3454; B65H 45/00
USPC ............... 493/374, 393, 416, 437, 454, 8, 23, 493/405, 413, 414, 417, 419, 426, 379, 386, 493/343, 344, 423; 156/66; 53/429, 439; 223/37, 38; 270/32, 45, 49, 50
See application file for complete search history.

(56) References Cited

U.S. PATENT DOCUMENTS

| | | | |
|---|---|---|---|
| 3,772,120 A | 11/1973 | Radzins | |
| 3,860,003 A | 1/1975 | Buell | |
| 4,519,596 A | 5/1985 | Johnson et al. | |
| 4,610,678 A | 9/1986 | Weisman et al. | |
| 4,614,512 A * | 9/1986 | Capdeboscq | ............... 493/441 |
| 4,648,336 A * | 3/1987 | Ragnebring | ............... 112/147 |
| 4,650,173 A | 3/1987 | Johnson et al. | |
| 4,673,402 A | 6/1987 | Weisman et al. | |
| 4,695,278 A | 9/1987 | Lawson | |

(Continued)

OTHER PUBLICATIONS

PCT International Search Report dated Feb. 23, 2012, 11 pages.

*Primary Examiner* — Thanh Truong
*Assistant Examiner* — Joy N Sanders
(74) *Attorney, Agent, or Firm* — Charles R. Matson (57) ABSTRACT

Aspects of the methods herein relate to the fabrication of diaper pants wherein side panels connected with the first waist region of a discrete chassis are conveyed in a first direction until a second waist region advances past a nip. The crotch region of the chassis is then redirected into the nip, folding the chassis to position the second waist region into a facing relationship with the first waist region. The folded chassis is then conveyed in a second direction with the side panels positioned on panel conveyors extending laterally outward from the first waist region. As the folded chassis travels in the second direction, the panel conveyors twist to position end regions of the side panels to connect with the second waist region of the folded chassis. The side panels and the waist regions of the folded chassis may also be compressed between the panel conveyors and a roller.

20 Claims, 8 Drawing Sheets

(56) References Cited

U.S. PATENT DOCUMENTS

| | | | |
|---|---|---|---|
| 4,704,115 A | 11/1987 | Buell | |
| 4,795,454 A | 1/1989 | Dragoo | |
| 4,834,735 A | 5/1989 | Alemany et al. | |
| 4,888,231 A | 12/1989 | Angstadt | |
| 4,909,803 A | 3/1990 | Aziz et al. | |
| 5,562,646 A | 10/1996 | Goldman et al. | |
| 5,599,335 A | 2/1997 | Goldman et al. | |
| 5,628,097 A | 5/1997 | Benson et al. | |
| 5,669,894 A | 9/1997 | Goldman et al. | |
| 5,904,802 A * | 5/1999 | Niedermeyer | 156/479 |
| 5,916,661 A | 6/1999 | Benson et al. | |
| 6,017,406 A | 1/2000 | Vogt | |
| 6,107,539 A | 8/2000 | Palumbo et al. | |
| 6,545,197 B1 | 4/2003 | Muller et al. | |
| 6,565,501 B1 * | 5/2003 | Trennepohl | 493/423 |
| 6,708,855 B2 | 3/2004 | Wilson et al. | |
| 6,790,798 B1 | 9/2004 | Suzuki et al. | |
| 7,452,320 B2 * | 11/2008 | Csida et al. | 493/418 |
| 7,521,587 B2 | 4/2009 | Busam et al. | |
| 7,617,656 B2 | 11/2009 | Wiedmann | |
| 8,273,003 B2 * | 9/2012 | Umebayashi et al. | 493/417 |
| 2002/0119878 A1 * | 8/2002 | Stopher | 493/374 |
| 2004/0158212 A1 | 8/2004 | Ponomarenko et al. | |
| 2006/0063657 A1 * | 3/2006 | St. Germain et al. | 493/418 |
| 2006/0108054 A1 | 5/2006 | Ukegawa | |
| 2008/0099130 A1 | 5/2008 | Umebayashi et al. | |
| 2009/0312730 A1 | 12/2009 | LaVon et al. | |
| 2010/0012285 A1 * | 1/2010 | Wiedmann | 162/252 |
| 2010/0049155 A1 | 2/2010 | Söderbergh et al. | |

* cited by examiner

METHOD AND APPARATUS FOR ASSEMBLING AND FOLDING ABSORBENT ARTICLES

CROSS REFERENCE TO RELATED APPLICATION

This application claims the benefit of U.S. Provisional Application No. 61/424,720, filed on Dec. 20, 2010, which is incorporated herein by reference.

FIELD OF THE INVENTION

The present disclosure relates to methods for manufacturing diaper pants having first and second side panels connecting opposing waist regions of a chassis, and more particularly, to methods for folding a chassis and connecting side panels with opposing waist regions.

BACKGROUND OF THE INVENTION

Along an assembly line, various types of articles, such as for example, diapers and other absorbent articles, may be assembled by adding components to and/or otherwise modifying an advancing, continuous web of material. For example, in some processes, advancing webs of material are combined with other advancing webs of material. In other examples, individual components created from advancing webs of material are combined with advancing webs of material, which in turn, are then combined with other advancing webs of material. In some cases, individual components created from advancing web or webs are combined with other individual components created from other advancing web or webs. Webs of material and component parts used to manufacture diapers may include: backsheets, topsheets, leg cuffs, waist caps, absorbent core components, front and/or back ears, fastening components, and various types of elastic webs and components such as leg elastics, barrier leg cuff elastics, stretch side panels, and waist elastics. Once the desired component parts are assembled, the advancing web(s) and component parts are subjected to a final knife cut to separate the web(s) into discrete diapers or other absorbent articles.

After the final knife cut, absorbent articles may also undergo a folding process prior to packaging. Diaper pants may also include additional manufacturing steps not used in the manufacture of conventional taped diapers. For example, diaper pants may include side panels that connect front and rear waist regions with each other. Thus, after being folded into a U about a lateral centerline in the same or similar way as conventional diapers, the side panels on diaper pants may connect the front and rear waist regions to form a waist opening and a pair of leg openings.

Some currently available folding and side panel connection apparatuses and processes involve mechanisms with complex multi-station folding and side panel seaming devices. Relatively less complex apparatuses and methods for chassis folding and side panel connections may be desirable.

SUMMARY OF THE INVENTION

The present disclosure relates to methods for manufacturing diaper pants. Aspects of the methods according to the present disclosure relate to the fabrication of diaper pants wherein first and second side panels connected with the first waist region of a discrete chassis are conveyed in a first direction until a second waist region advances past a nip. The crotch region of the chassis is then redirected into the nip, thus folding the chassis to position the second waist region into a facing relationship with the first waist region. The folded chassis is then conveyed in a second direction with the first and second side panels positioned on first and second panel conveyors extending laterally outward from the first waist region. As the folded chassis travels in the second direction, the first and second panel conveyors twist to position end regions of the side panels in contact with and/or connect with the second waist region of the folded chassis. In some embodiments, the end regions of the side panels and the waist regions of the folded chassis may also be compressed between the first and second panel conveyors and a roller.

In one form, a method may be configured for assembling disposable diaper pants, each diaper pant including a chassis, a first side panel, and a second side panel, each chassis comprising a topsheet, a backsheet, and an absorbent core disposed between the topsheet and the backsheet, each chassis having a first waist region longitudinally opposed to a second waist region, and a crotch region located between the first and second waist regions, and having a longitudinal axis and a lateral axis, the first and second side panels joining the first waist region and the second waist region to form a waist opening and a pair of leg openings. The method includes the steps of: connecting first end regions of the first and second side panels with the first waist region of the chassis; conveying the chassis in a first direction, wherein the backsheet is in direct contact with a moving surface of a first chassis conveyor, and wherein the first and second side panels extend laterally outward from the first waist region with the first side panel positioned on a moving surface of a first panel conveyor and the second side panel positioned on a moving surface of a second panel conveyor; advancing the second waist region of the chassis past a nip defined between the first chassis conveyor and a second chassis conveyor; folding the chassis to position the second waist region into a facing relationship with the first waist region by redirecting the crotch region of the chassis into the nip; conveying the folded chassis in a second direction between the first chassis conveyor and the second chassis conveyor, wherein the first and second side panels extend laterally outward from the first waist region with the first side panel positioned on the moving surface of the first panel conveyor and the second side panel positioned on the moving surface of the second panel conveyor; twisting the first and second panel conveyors to position second end regions of the first and second side panels in contact with the second waist region of the chassis; connecting the second end regions of the first and second side panels with the second waist region of the chassis; and compressing the second end regions of the first and second side panels and the second waist region between the moving surface of the first and second panel conveyors and a first roller.

In another form, a method may be configured for assembling disposable diaper pants, each diaper pant comprising a chassis, a first side panel, and a second side panel, each chassis comprising a topsheet, a backsheet, and an absorbent core disposed between the topsheet and the backsheet, each chassis having a first waist region longitudinally opposed to a second waist region, and a crotch region located between the first and second waist regions, and having a longitudinal axis and a lateral axis, the first and second side panels joining the first waist region and the second waist region to form a waist opening and a pair of leg openings. The method includes the steps of: connecting first end regions of the first and second side panels with the first waist region of the chassis; conveying the chassis, first side panel, and second side panel in a first direction on a carrier; advancing the second waist region of the chassis past a nip defined between a first chassis conveyor and a second chassis conveyor; transferring the chassis from: the carrier to the first and second chassis conveyor, the first side panel to a first panel conveyor, and the second side panel to a second panel conveyor, wherein the backsheet is in direct contact with a moving surface of the first chassis conveyor, and wherein the first and second side panels extend laterally outward from the first waist region with the first side panel positioned on a moving surface of the first panel conveyor and the second side panel positioned on a moving surface of the second panel conveyor; folding the chassis to position the second waist region into a facing relationship with the first waist region by redirecting the crotch region of the chassis into the nip; conveying the folded chassis in a second direction between the first chassis conveyor and the second chassis conveyor, wherein the first and second side panels extend laterally outward from the first waist region with the first side panel positioned on the moving surface of the first panel conveyor and the second side panel positioned on the moving surface of the second panel conveyor; twisting the first and second panel conveyors to position second end regions of the first and second side panels in contact with the second waist region of the chassis; connecting the second end regions of the first and second side panels with the second waist region of the chassis.

DETAILED DESCRIPTION OF THE INVENTION

The following term explanations may be useful in understanding the present disclosure:

"Absorbent article" is used herein to refer to consumer products whose primary function is to absorb and retain soils and wastes. "Diaper" is used herein to refer to an absorbent article generally worn by infants and incontinent persons about the lower torso. The term "disposable" is used herein to describe absorbent articles which generally are not intended to be laundered or otherwise restored or reused as an absorbent article (e.g., they are intended to be discarded after a single use and may also be configured to be recycled, composted or otherwise disposed of in an environmentally compatible manner).

The term "disposed" is used herein to mean that an element(s) is formed (joined and positioned) in a particular place or position as a macro-unitary structure with other elements or as a separate element joined to another element.

As used herein, the term "joined" encompasses configurations whereby an element is directly secured to another element by affixing the element directly to the other element, and configurations whereby an element is indirectly secured to another element by affixing the element to intermediate member(s) which in turn are affixed to the other element.

"Longitudinal" means a direction running substantially perpendicular from a waist edge to a longitudinally opposing waist edge of an absorbent article when the article is in a flat out, uncontracted state, or from a waist edge to the bottom of the crotch, i.e. the fold line, in a bi-folded article. Directions within 45 degrees of the longitudinal direction are considered to be "longitudinal." "Lateral" refers to a direction running from a longitudinally extending side edge to a laterally opposing longitudinally extending side edge of an article and generally at a right angle to the longitudinal direction. Directions within 45 degrees of the lateral direction are considered to be "lateral."

The term "substrate" is used herein to describe a material which is primarily two-dimensional (i.e. in an XY plane) and whose thickness (in a Z direction) is relatively small (i.e. 1/10 or less) in comparison to its length (in an X direction) and width (in a Y direction). Non-limiting examples of substrates include a web, layer or layers or fibrous materials, nonwovens, films and foils such as polymeric films or metallic foils. These materials may be used alone or may comprise two or more layers laminated together. As such, a web is a substrate.

The term "nonwoven" refers herein to a material made from continuous (long) filaments (fibers) and/or discontinuous (short) filaments (fibers) by processes such as spunbonding, meltblowing, carding, and the like. Nonwovens do not have a woven or knitted filament pattern.

The term "machine direction" (MD) is used herein to refer to the direction of material flow through a process. In addition, relative placement and movement of material can be described as flowing in the machine direction through a process from upstream in the process to downstream in the process.

The term "cross direction" (CD) is used herein to refer to a direction that is generally perpendicular to the machine direction.

The term "pant" (also referred to as "training pant", "pre-closed diaper", "diaper pant", "pant diaper", and "pull-on diaper") refers herein to disposable absorbent articles having a continuous perimeter waist opening and continuous perimeter leg openings designed for infant or adult wearers. A pant can be configured with a continuous or closed waist opening and at least one continuous, closed, leg opening prior to the article being applied to the wearer.

The present disclosure relates to methods for manufacturing absorbent articles, and in particular, methods for making diaper pants. As discussed in more detail below, diaper pants may include a chassis having a first waist region, a longitudinally opposed second waist region, and a crotch region located between the first and second waist regions. The chassis may also include a longitudinal axis and a lateral axis, wherein the longitudinal axis extends through the first and second waist regions. Each diaper pant may further include a first side panel and a second side panel connected with the first waist region and the second waist region defining a waist opening and leg openings. Aspects of the methods according to the present disclosure relate to the fabrication of diaper pants wherein first and second side panels connected with the first waist region of a discrete chassis are conveyed in a first direction until a second waist region advances past a nip. The crotch region of the chassis is then redirected into the nip, thus folding the chassis to position the second waist region into a facing relationship with the first waist region. The folded chassis is then conveyed in a second direction with the first and second side panels positioned on first and second panel conveyors extending laterally outward from the first waist region. As the folded chassis travels in the second direction, the first and second panel conveyors twist to position end regions of the side panels in contact with and/or connect with the second waist region of the folded chassis. In some embodiments, the end regions of the side panels and the waist regions of the folded chassis may also be compressed between the first and second panel conveyors and a roller.

The following provides a general description of various types of diaper pants that may be produced with the methods and apparatuses disclosed herein to help provide additional context to the subsequent discussion of the process embodiments.

Figure 1:
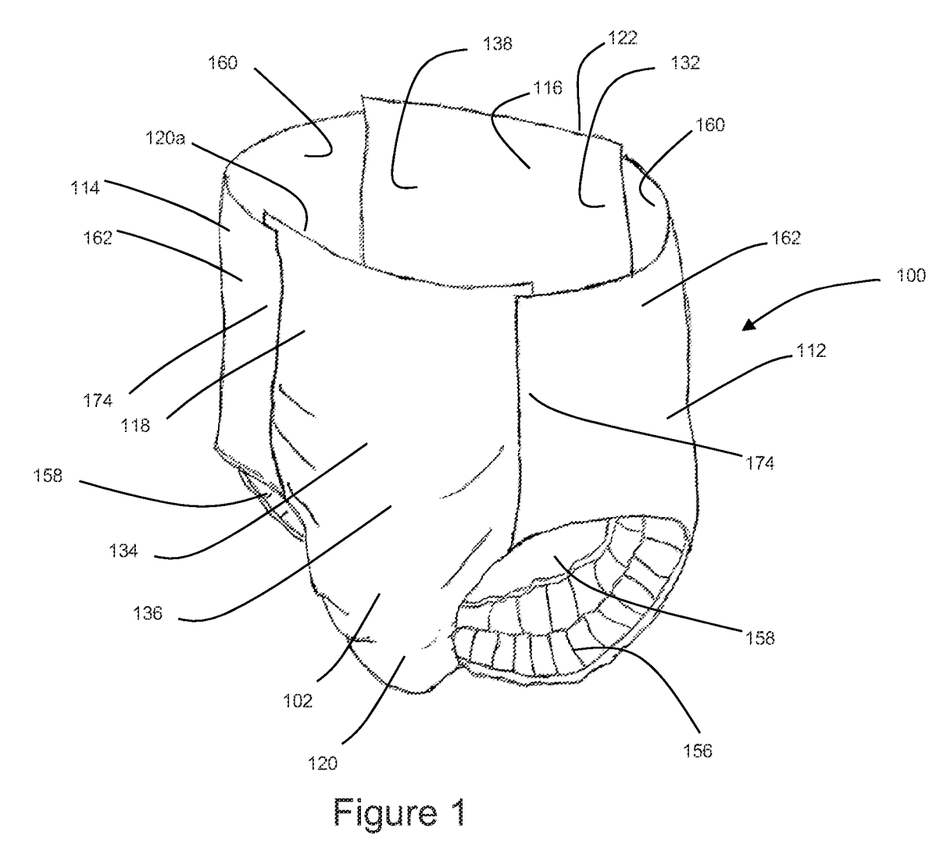
FIG. 1 is a perspective view of a refastenable pant diaper in a pre-fastened configuration.
Figure 2:
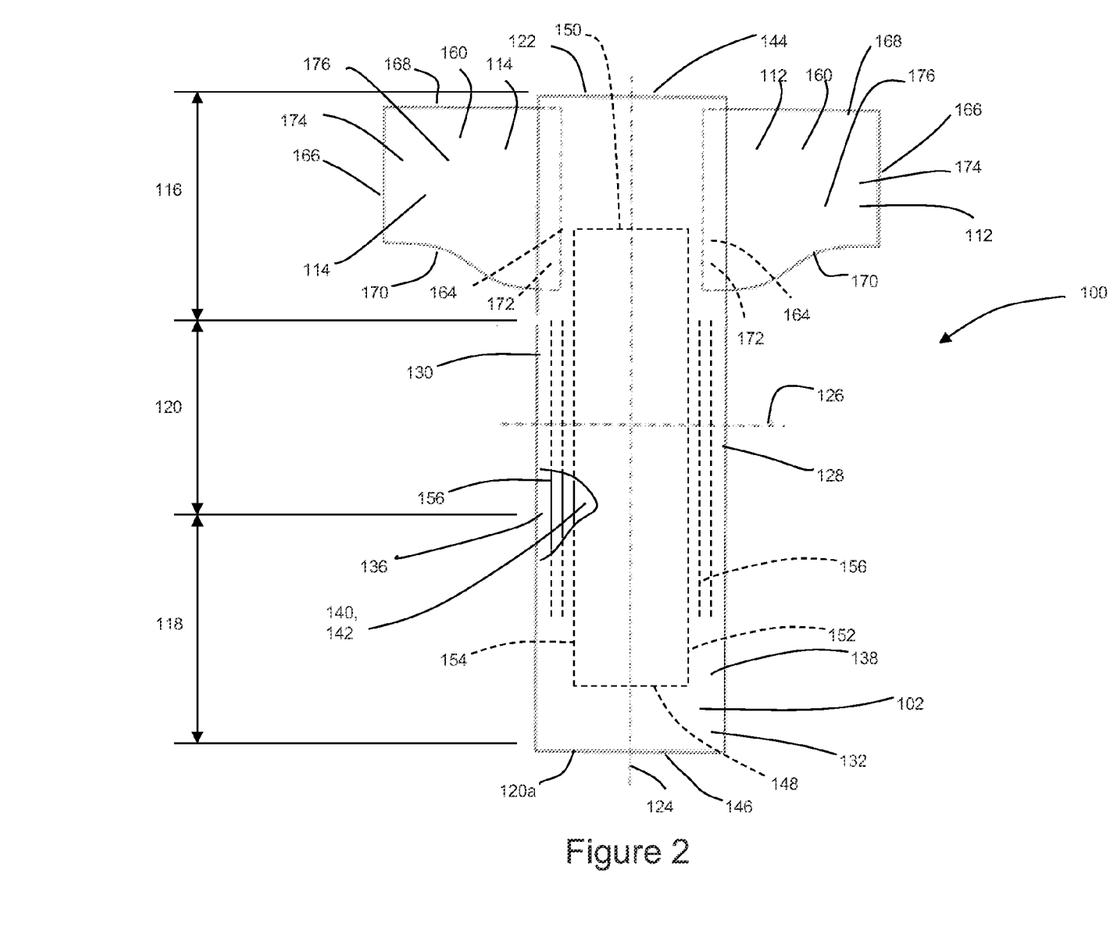
FIG. 2 is a partially cut away plan view of the diaper pant shown in FIG. 1 with side panels connected with the a waist region and extending laterally outward from the chassis.

FIGS. 1 and 2 show an example of a pant diaper 100 that may be constructed in accordance with the methods disclosed herein. In particular, FIG. 1 shows a perspective view of a pant diaper 100 in a pre-fastened configuration, and FIG. 2 shows a plan view of the pant diaper 100 with the portion of the diaper that faces toward a wearer oriented towards the viewer. The pant diaper 100 shown in FIGS. 1 and 2 includes a chassis 102, a first side panel 112, and a second side panel 114.

With continued reference to FIG. 2, the chassis 102 includes a first waist region 116, a second waist region 118, and a crotch region 120 disposed intermediate the first and second waist regions. The first waist region 116 may be configured as a back waist region, and the second waist region 118 may be configured as a front waist region. In some embodiments, the length of each of the front waist region, back waist region, and crotch region may be approximately ⅓ of the length of the absorbent article 100. The diaper 100 may also include a laterally extending front waist edge 120a in the front waist region 118 and a longitudinally opposing and laterally extending back waist edge 122 in the back waist region 116. To provide a frame of reference for the present discussion, the diaper 100 and chassis 102 of FIG. 2 is shown with a longitudinal axis 124 and a lateral axis 126. In some embodiments, the longitudinal axis 124 may extend through the front waist edge 120a and through the back waist edge 122. And the lateral axis 126 may extend through a first longitudinal or right side edge 128 and through a midpoint of a second longitudinal or left side edge 130 of the chassis 102.

As shown in FIGS. 1 and 2, the pant diaper 100 may include an inner, body facing surface 132, and an outer, garment facing surface 134. The chassis 102 may include a backsheet 136 and a topsheet 138. An absorbent assembly 140 including an absorbent core 142 may be disposed between a portion of the topsheet 138 and the backsheet 136. As discussed in more detail below, the diaper 100 may also include other features, such as leg elastics and/or leg cuffs to enhance the fit around the legs of the wearer.

As shown in FIG. 2, the periphery of the chassis 102 may be defined by the first longitudinal side edge 128, a second longitudinal side edge 130; a first laterally extending end edge 144 disposed in the first waist region 116; and a second laterally extending end edge 146 disposed in the second waist region 118. Both side edges 128 and 130 extend longitudinally between the front waist edge 120a and the back waist edge 122. The laterally extending end edges 144 and 146 of the chassis may form a portion of the laterally extending front waist edge 120a in the front waist region 116 and a portion of the longitudinally opposing and laterally extending back waist edge 122 in the back waist region 118. When the pant diaper 100 is worn on the lower torso of a wearer, the front waist edge 120a and the back waist edge 122 of the chassis 102 may encircle a portion of the waist of the wearer. At the same time, the chassis side edges 128 and 130 may encircle at least a portion of the legs of the wearer. And the crotch region 120 may be generally positioned between the legs of the wearer with the absorbent core 142 extending from the front waist region 118 through the crotch region 120 to the back waist region 116.

It is to also be appreciated that a portion or the whole of the diaper 100 may also be made laterally extensible. The additional extensibility may help allow the diaper 100 to conform to the body of a wearer during movement by the wearer. The additional extensibility may also help, for example, allow the user of the diaper 100 including a chassis 102 having a particular size before extension to extend the front waist region 118, the back waist region 116, or both waist regions of the diaper 100 and/or chassis 102 to provide additional body coverage for wearers of differing size, i.e., to tailor the diaper to an individual wearer. Such extension of the waist region or regions may give the absorbent article a generally hourglass shape, so long as the crotch region is extended to a relatively lesser degree than the waist region or regions, and may impart a tailored appearance to the article when it is worn.

As previously mentioned, the pant diaper 100 may include a backsheet 136. The backsheet 136 may also define the outer surface 134 of the chassis 102. The backsheet 136 may be impervious to fluids (e.g., menses, urine, and/or runny feces) and may be manufactured from a thin plastic film, although other flexible liquid impervious materials may also be used. The backsheet 136 may prevent the exudates absorbed and contained in the absorbent core from wetting articles which contact the diaper 100, such as bedsheets, pajamas and undergarments. The backsheet 136 may also comprise a woven or nonwoven material, polymeric films such as thermoplastic films of polyethylene or polypropylene, and/or a multi-layer or composite materials comprising a film and a nonwoven material (e.g., having an inner film layer and an outer nonwoven layer). The backsheet may also comprise an elastomeric film. An example backsheet 140 may be a polyethylene film having a thickness of from about 0.012 mm (0.5 mils) to about 0.051 mm (2.0 mils). Exemplary polyethylene films are manufactured by Clopay Corporation of Cincinnati, Ohio, under the designation BR-120 and BR-121 and by Tredegar Film Products of Terre Haute, Ind., under the designation XP-39385. The backsheet 136 may also be embossed and/or matte-finished to provide a more clothlike appearance. Further, the backsheet 136 may permit vapors to escape from the absorbent core (i.e., the backsheet is breathable) while still preventing exudates from passing through the backsheet 136. The size of the backsheet 136 may be dictated by the size of the absorbent core 142 and/or particular configuration or size of the diaper 100.

Also described above, the pant diaper 100 may include a topsheet 138. The topsheet 138 may also define all or part of the inner surface 132 of the chassis 102. The topsheet 138 may be compliant, soft feeling, and non-irritating to the wearer's skin. It may be elastically stretchable in one or two directions. Further, the topsheet 138 may be liquid pervious, permitting liquids (e.g., menses, urine, and/or runny feces) to penetrate through its thickness. A topsheet 138 may be manufactured from a wide range of materials such as woven and nonwoven materials; apertured or hydroformed thermoplastic films; apertured nonwovens, porous foams; reticulated foams; reticulated thermoplastic films; and thermoplastic scrims. Woven and nonwoven materials may comprise natural fibers such as wood or cotton fibers; synthetic fibers such as polyester, polypropylene, or polyethylene fibers; or combinations thereof. If the topsheet 138 includes fibers, the fibers may be spunbond, carded, wet-laid, meltblown, hydroentangled, or otherwise processed as is known in the art.

Topsheets 138 may be selected from high loft nonwoven topsheets, apertured film topsheets and apertured nonwoven topsheets. Apertured film topsheets may be pervious to bodily exudates, yet substantially non-absorbent, and have a reduced tendency to allow fluids to pass back through and rewet the wearer's skin. Exemplary apertured films may include those described in U.S. Pat. Nos. 5,628,097; 5,916,661; 6,545,197; and 6,107,539.

As mentioned above, the pant diaper 100 may also include an absorbent assembly 140 that is joined to the chassis 102. As shown in FIG. 2, the absorbent assembly 140 may have a laterally extending front edge 148 in the front waist region 116 and may have a longitudinally opposing and laterally extending back edge 150 in the back waist region 118. The absorbent assembly may have a longitudinally extending right side edge 152 and may have a laterally opposing and longitudinally extending left side edge 154, both absorbent assembly side edges 152 and 154 may extend longitudinally between the front edge 148 and the back edge 150. The absorbent assembly 140 may additionally include one or more absorbent cores 142 or absorbent core layers. The absorbent core 142 may be at least partially disposed between the topsheet 138 and the backsheet 136 and may be formed in various sizes and shapes that are compatible with the diaper 100. Exemplary absorbent structures for use as the absorbent core of the present disclosure are described in U.S. Pat. Nos. 4,610,678; 4,673,402; 4,888,231; and 4,834,735.

Some absorbent core embodiments may comprise fluid storage cores that contain reduced amounts of cellulosic airfelt material. For instance, such cores may comprise less than about 40%, 30%, 20%, 10%, 5%, or even 1% of cellulosic airfelt material. Such a core may comprises primarily absorbent gelling material in amounts of at least about 60%, 70%, 80%, 85%, 90%, 95%, or even about 100%, where the remainder of the core comprises a microfiber glue (if applicable). Such cores, microfiber glues, and absorbent gelling materials are described in U.S. Pat. Nos. 5,599,335; 5,562,646; 5,669,894; and 6,790,798 as well as U.S. Patent Publication Nos. 2004/0158212 and 2004/0097895.

As previously mentioned, the diapers 100 may also include elasticized leg cuffs 156. It is to be appreciated that the leg cuffs 156 can be and are sometimes also referred to as leg bands, side flaps, barrier cuffs, elastic cuffs or gasketing cuffs. The elasticized leg cuffs 156 may be configured in various ways to help reduce the leakage of body exudates in the leg regions. Example leg cuffs 156 may include those described in U.S. Pat. Nos. 3,860,003; 4,909,803; 4,695,278; 4,795,454; 4,704,115; 4,909,803; and U.S. Patent Publication No. 2009/0312730A1.

As mentioned above, pant diapers may be manufactured and provided to consumers in a configuration wherein the front waist region and the back waist region are pre-fastened or connected to each other as packaged, prior to being applied to the wearer. For example, the pant diaper 100 may be folded about a lateral centerline with the interior surface 132 of the first waist region 116 in surface to surface contact with the interior surface 132 of the second waist region 118. As such, pant diapers may have a continuous perimeter waist opening 157 and continuous perimeter leg openings 158 designed for infant or adult wearers, such as shown in FIG. 1. As discussed in more detail below, a diaper pant can be preformed by various techniques including, but not limited to, joining together portions of the diaper using refastenable and/or permanent closure members (e.g., seams, heat bonds, pressure welds, adhesives, cohesive bonds, mechanical fasteners, etc.). In addition, pant diapers can be preformed anywhere along the circumference of the waist region (e.g., side fastened or connected, front waist fastened or connected, rear waist fastened or connected).

As previously mentioned, pant diapers may be configured with side panels connected with the chassis in one or both of the waist regions. For example, the pant diaper 100 shown in FIGS. 1 and 2 includes a first side panel 112 and a second side panel 114. The first and second side panels 112, 114 are connected with the first waist region 116 and the second waist region 118. It is to be appreciated that the first side panel 112 and/or the second side panel 114 may be permanently and/or refastenably connected with the chassis 102. For example, in some embodiments, the first side panel 112 and the second side panel 114 are permanently connected with the first waist region 116 and the second waist region 118. In some embodiments, the first side panel 112 and the second side panel 114 are refastenably connected with the first waist region 116 and permanently connected with the second waist region 118. In other embodiments, the first side panel 112 and the second side panel 114 are permanently connected with the first waist region 116 and refastenably connected with the second waist region 118. In yet other embodiments, the first side panel 112 and the second side panel 114 are refastenably connected with the first waist region 116 and the second waist region 118.

As such, it is to be appreciated that the side panels 112, 114 may be connected with the chassis in various ways. For example, the proximal regions and/or distal regions of the side panels disposed in one or both of the waist regions may be permanently bonded, releasably connected, and/or refastenably connected with the chassis and/or each other, with for example, adhesives, cohesives, thermal bonding, ultrasonic bonding, mechanical bonding and mechanical fastening e.g. hook and loop type fasteners, macrofasteners, buttons, snaps, tab and slot fasteners, tape fasteners, adhesive fasteners, cohesive fasteners, magnetic fasteners, hermaphrodidic fasteners, and the like.

For example, one or more fastener elements may be located on the side panels and may be adapted to refastenably connect with one or more corresponding fastening elements located in the first or second waist regions or alternatively the fastener elements may be adapted to refastenably connect with one or more components of the absorbent article including the side panels.

As shown in FIGS. 1 and 2, the first side panel 112 and the second side panel 114 each include a first surface 160 defining an inner, body facing surface, and an opposing second surface 162, defining an outer, garment facing surface. The perimeter of the first and second side panels may each be defined by a first edge 164, a second edge 166, a third edge 168, and a fourth edge 170. As such, the first and second side panels 112, 114 may also each include a first end region 172 extending along the first edge 164, a second end region 174 extending along the second edge 166, and a central region 176 between the first and second end regions 172, 174. The first end regions 172 of the first and second side panels 112, 114 may be connected with the first waist region 116 of the chassis 102, and the second end regions 174 of the first and second side panels 112, 114 may be connected with the second waist region 118 of the chassis 102. It should also be appreciated that either end regions 172, 174 of the side panels 112, 114 may be connected with either the inner, body facing surface 132 or the outer, garment facing surface 134 of the chassis 102 along either the first or second waist regions 116, 118.

It should be appreciated that although the absorbent article 100 shown in FIGS. 1 and 2 includes side panels 112, 114 defined by two separate and discrete pieces of material connected with the second waist region 118, the absorbent article may be configured with first and second side panels 112, 114 defined by opposing end regions of a continuous belt that is connected with the chassis 102 along the second waist region 118. It should also be appreciated that such a continuous belt may be connected with either the inner, body facing surface 132 or the outer, garment facing surface 134 of the chassis 102 along the second waist region 118. The side panels may also be defined by the combination of two or more discrete pieces of material. The side panels 112, 114 may be substantially rectangular in shape or the side panels may be shaped in such a way as to provide an integral tab for ease of opening and refastening. The side panels may also be extensible in at least the lateral direction. The side panels may also be elastically extensible in the lateral direction. Furthermore, the side panels may be elastically extensible in both the longitudinal and lateral directions. The side panels may comprise a film, a nonwoven or a combination of film and nonwoven. The side panels may also comprise a plurality of strand-like filaments and a nonwoven. The strand-like elements may also be elastically extensible in at least the lateral direction.

It is to be appreciated that the side panels 112, 114 may include various types of materials, such as disclosed with respect to the elastic belts described in U.S. Pat. No. 7,569,039, which is hereby incorporated by reference herein. For example, the side panels may include plastic films; apertured plastic films; nonwoven or nonwoven webs of natural materials (e.g., wood or cotton fibers); synthetic fibers (e.g. polyolefins, polyamides, polyester, polyethylene, and/or polypropylene fibers); or combinations of natural and/or synthetic fibers; or coated woven or nonwoven webs. In some embodiment, the side panels may include a stretchable nonwoven. In other embodiments, the side panels may include an inner hydrophobic non-stretchable nonwoven material and an outer hydrophobic, non-stretchable nonwoven material. In addition, the side panels may include waist elastic material and side elastic material including one or more of elastic elements such as strand or panels extending in a transverse direction. The side panel elastic material may also be interposed between an outer layer and inner layer.

It should also be appreciated that the side panels in one waist region may have the same lateral extent from the side edge of the chassis to the distal edge of the side panel as the longitudinally opposed side panels in the opposite waist region or alternatively the side panels disposed in a first waist region may have different lateral extent as measured from the side edge of the chassis to the distal edge of the side panel than the side panels disposed in a second waist region.

Figure 3:
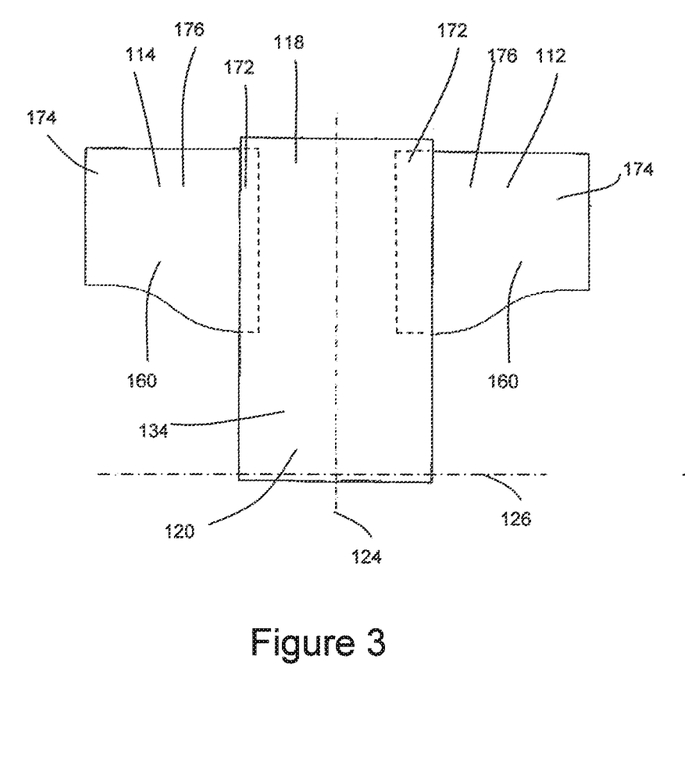
FIG. 3 is a view of the diaper shown in FIG. 2 with the chassis folded about a lateral axis.
Figure 4:
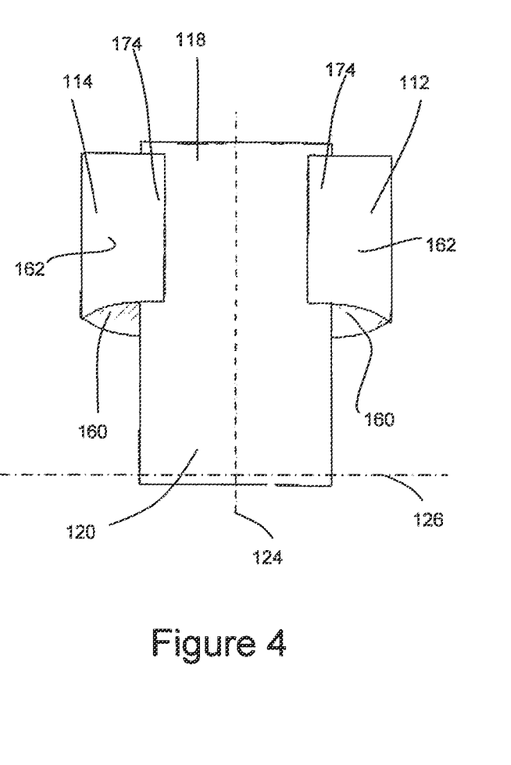
FIG. 4 is a view of the diaper shown in FIG. 3 with the side panels folded and connected with an opposing waist region of the chassis.

As previously mentioned, the apparatuses and methods according to the present disclosure may be utilized to assemble and fold pant diapers 100. More particularly, the methods and apparatuses may be configured to advance a chassis 102 having first and second side panels 112, 114 connected with the first or second waist region 116, 118; fold the chassis 102 along a lateral axis; and fold and connect the first and second side panels 112, 114 with the opposing waist region of the chassis 102. The following discussion of the methods and apparatus will also refer to FIGS. 2-4, which show a pant diaper 100 in different stages of assembly. As mentioned above, FIG. 2 shows a plan view of the pant diaper 100 with the inner, body facing surface 132 of the chassis oriented towards the viewer. The first end regions 172 of the first and second side panels 112, 114 are connected with the first waist region 116 of the chassis 102. And the first and second side panels 112, 114 extend laterally outward from the chassis 102 to the second end regions 174. FIG. 3 shows the pant diaper 100 of FIG. 2 after the chassis 102 has been folded along a lateral axis 126 to bring the first waist region 116 and the second waist region 118 into a facing relationship. And FIG. 4 shows the pant diaper 100 of FIG. 3 after the first and second side panels 112, 114 have been folded around central regions 176 and the second end regions 174 have been connected with the outer, garment facing surface 134 of the chassis 102 in the second waist region 118.

FIGS. 5-9 show a various views of a converting apparatus 300 adapted to manufacture pant diapers 100. The method of operation of the converting apparatus 300 may be described with reference to the various components of pant diapers 100 described above and shown in FIGS. 1-4. As shown in FIGS. 5-9, a pant diaper 100 including a chassis 102, a first side panel 112, and a second side panel 114 are conveyed in a first machine direction MD1 with the chassis 102 in a flat out, uncontracted state with the side panels 112, 114 extending laterally outward in a cross direction CD from the first waist region 116. At this point in the process, only the first end regions 172 of the side panels 112, 114 are connected with the chassis 102. The pant diaper 100 is advanced in the first direction MD1 so that the second waist region 118 of the chassis 102 advances past a nip 302. The crotch region 120 is redirected into the nip 302, causing the chassis 102 to fold about a lateral axis 126 in the crotch region 120 to place the first and second waist regions 116, 118 into a facing relationship. More particularly, the chassis 102 is folded such that the inner surface 132 of the chassis 102 in the first waist region 116 is placed in a facing relationship with the inner surface 132 of the chassis 102 in the second waist region 118. From the nip 302, the folded chassis 102 is conveyed in a second machine direction MD2. As the chassis 102 advances in the second machine direction MD2, the first and second side panels 112, 114 are folded around central regions 176 to place the second end regions 174 of the side panels 112, 114 into contact with and to connect with the second waist region 118 of the chassis 102. The pant diaper 100 is then redirected to advance in a third machine direction MD3. As discussed in more detail below, as the pant diaper 100 is redirected from the second direction MD2 to the third direction MD3, the connections between second end regions 174 of the side panels 112, 114 and the second waist region 118 may be compressed between a roller and belts.

The converting apparatus 300 includes a plurality of conveyors arranged to convey the pant diaper in the aforementioned machine directions, fold the chassis, as well as fold and connect the side panels with the folded chassis. With reference to FIGS. 5-9, the converting apparatus 300 may include a first panel conveyor 304, a second panel conveyor 306, a first chassis conveyor 308, and a second chassis conveyor 310. The panel conveyors 304, 306 and the first chassis conveyor 308 may each include a belt 312 routed in an endless loop around four rollers 314. And the first chassis conveyor 308 is located between the panel conveyors 304, 306 in the cross direction CD. The second chassis conveyor 310 may include a belt 312 routed in an endless loop around six rollers 315. As discussed in more detail below, the first and second chassis conveyors 308, 310 help support, convey, and fold the chassis, while the panel conveyors 304, 306 help support, convey, and fold the side panels 112, 114. In order to overcome problems associated with the uncontrolled movement of the chassis 102 and side panels 112, 114 during conveyance, the conveyors 304, 306, 310, 312 may include a vacuum system in communication with a porous belt or other foraminous surface that allows the suction force of the vacuum system to be exerted on chassis and/or side panels.

As shown in FIGS. 5-9, the belts 312 of the first chassis conveyor 308 and the panel conveyors 304, 306 extend along the first machine direction MD1 to a first roller 314a. The three belts 312 of the conveyors 304, 306, 308 partially wrap around the first roller 314a and extend in the second machine direction MD2 and partially wrap around a second roller 314b. From the second roller 314b, the three belts 312 of the conveyors 304, 306, 308 extend in the third machine direction MD3 and partially wrap around a third roller 314c. From the third roller 314c, the three belts 312 of the conveyors 304, 306, 308 extend to and partially wrap around a fourth roller 314d. From the fourth roller 314d, the three belts of the conveyors 304, 306, 308 again extend in the first machine direction MD1. Each belt 312 of the conveyors 304, 306, 308 includes a first surface 316 and a second surface 318 opposite the first surface 316. The first surface 316 of the belt 312 of the first chassis conveyor 308 is positioned to engage and convey the chassis 102, and the second surface of the 318 of the belt 312 of the first chassis conveyor is positioned to engage the outer surfaces of the four rollers 314. The first surfaces 316 of the belts 312 of the panel conveyors 304, 306 are positioned to engage and convey the first and second side panels 112, 114. The panel conveyors 304, 306 are also configured to fold the first and second side panels 112, 114 while the chassis 102 is conveyed in the second machine direction MD2. More particularly, the belts 312 of the first and second panel conveyors 304, 306 are twisted 180° in a first twist direction between the first roller 314a and the second roller 314b. Thus, the travel paths of the first surfaces 316 of the belts 312 the first and second panel conveyors 304, 306 causes the side panels 112, 114 to fold around the central regions 176 and position the second end regions 174 of the side panels 112, 114 in contact with the second waist region 118 of the chassis 102. As such, the second surfaces 318 of the belts 312 of the first and second conveyors 304, 306 engage the outer surface of the first roller 314a, and the first surfaces 316 of the belts 312 the first and second conveyors 304, 306 engage the outer surface of the second roller 314b. The twist is then removed from the belts 312 of the side panel conveyors 304, 306 along the third machine direction MD3. More particularly, the belts 312 of the first and second panel conveyors 304, 306 are twisted 180° in a second direction (opposite the first twist direction) between the second roller 314b and the third roller 314c. As such, the second surfaces 318 of belts 312 of the first and second conveyors 304, 306 engage the outer surface of the third roller 314c as well as the fourth roller 314d.

It is to be appreciated that the first chassis conveyor 308 and the panel conveyors 304, 306 can each be arranged and configured other ways than shown in FIGS. 5-9. For example, the conveyors 304, 306, 308 can include more than one belt and may include different numbers of rollers arranged in different ways.

Figure 5:
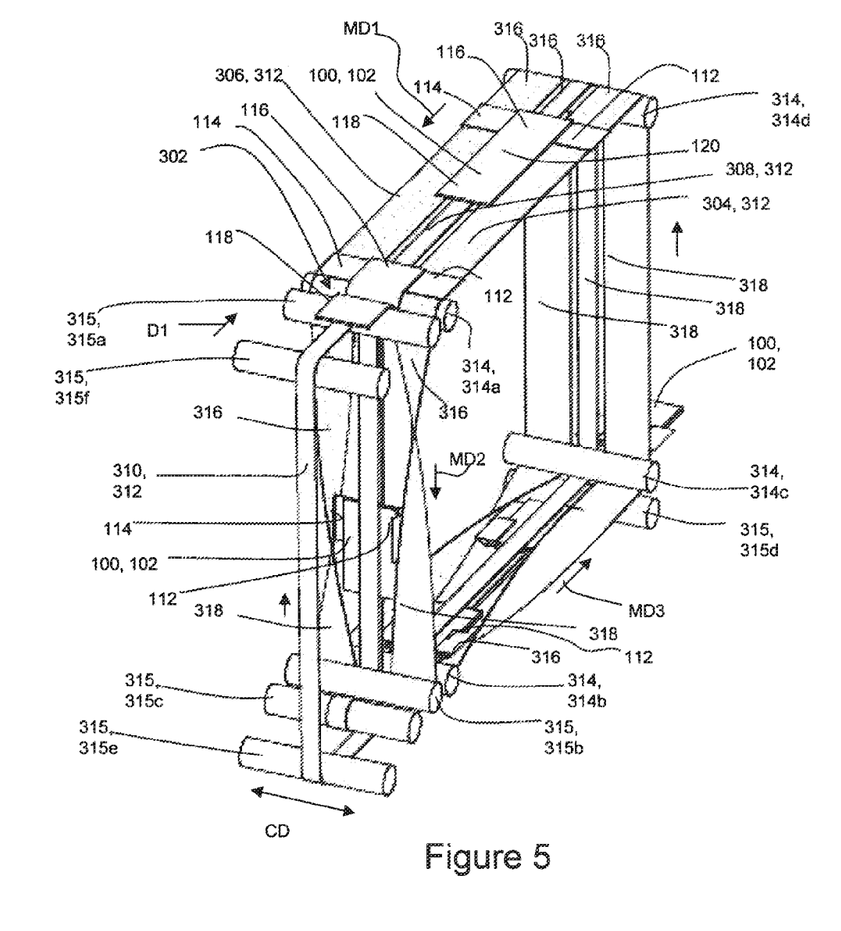
FIG. 5 is a right side isometric view of a converting apparatus configured to fold the chassis of a pant diaper and connect side panels with opposing waist regions.
Figure 6:
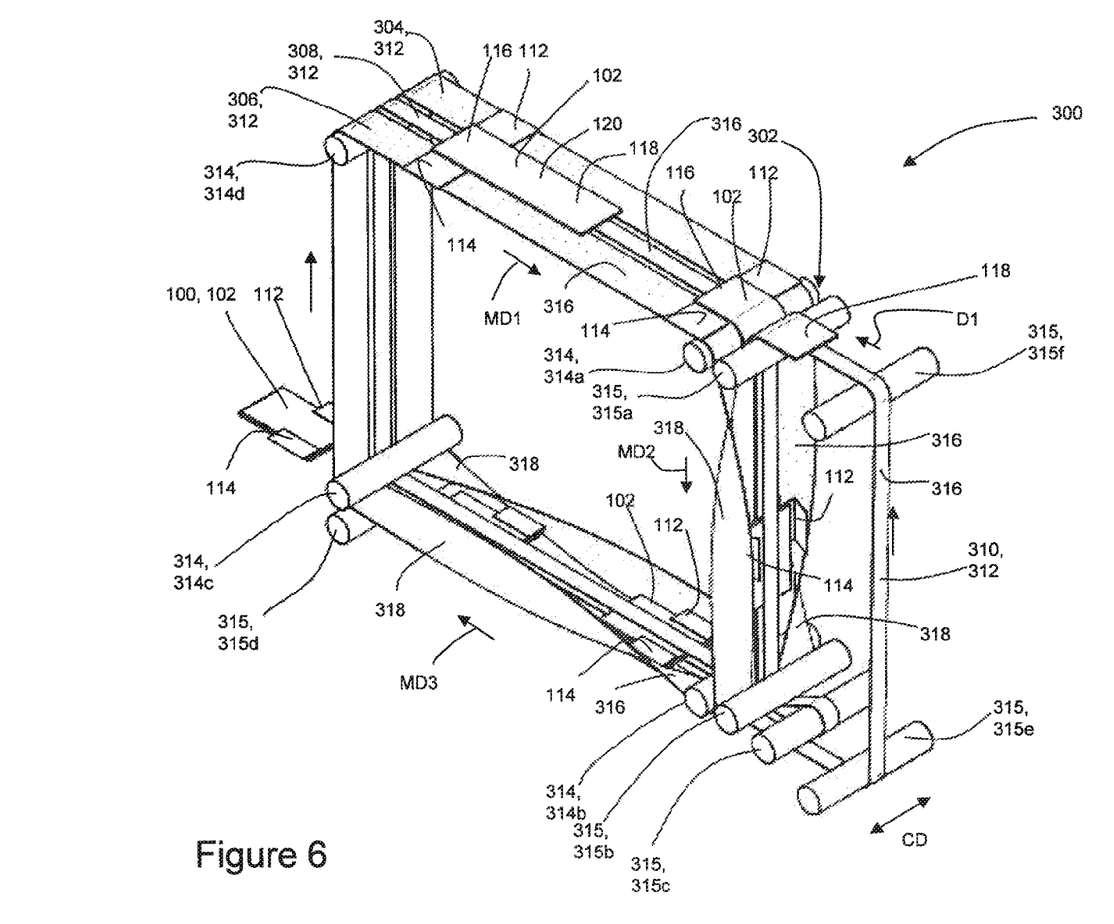
FIG. 6 is a left side isometric view of the converting apparatus of FIG. 5.
Figure 7:
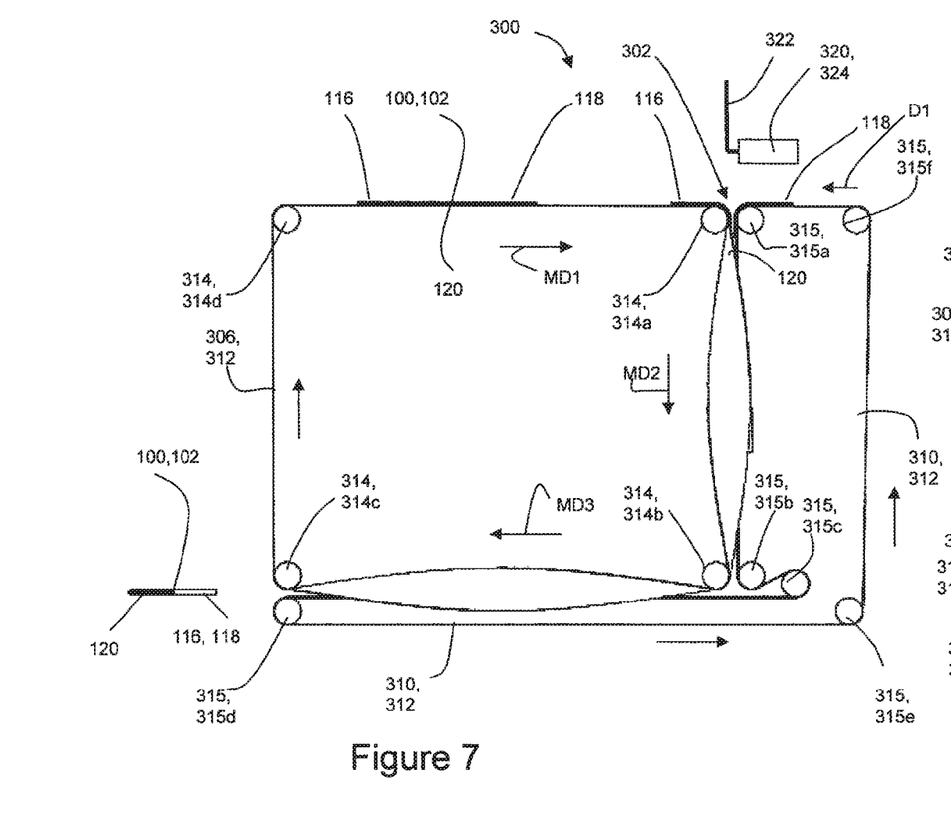
FIG. 7 is a left side view of the converting apparatus of FIG. 6.

As shown in FIGS. 5-9, the belt 312 of the second chassis conveyor 310 extends along a first direction D1 to a first roller 315a. As shown in FIGS. 5-7, first direction D1 may be opposite the first machine direction MD1. The distance between the belt 312 of the second chassis conveyor 310 at the first roller 315a and the belt 312 of the first chassis conveyor 308 at the first roller 314a defines nip 302. The belt 312 of the second chassis conveyor 310 partially wraps around the first roller 315a and extends in the second machine direction MD2 and partially wraps around a second roller 315b. From the second roller 315b, the belt 312 of the second chassis conveyor 310 extends to and partially wraps around a third roller 315c. From the third roller 315c, the belt 312 of the second chassis conveyor 310 extends in the third machine direction MD3 and partially wrap around a fourth roller 315d. From the fourth roller 315d, the belt 312 of the second chassis conveyor 310 extends to and partially wraps around a fifth roller 315e and extends to and partially wraps around a sixth roller 315f. From the sixth roller 315f, the belt 312 of the second chassis conveyor 310 again extends in the first machine direction D1. The belt 312 of the second chassis conveyor 310 also includes a first surface 316 and a second surface 318 opposite the first surface 316. The first surface 316 of the second chassis conveyor 310 is positioned to engage and convey the chassis 102 along the second machine direction MD2 and the third machine direction MD3. The first surface 316 of the second chassis conveyor 310 is also positioned to engage outer surfaces of the roller 315c. And the second surface of the 318 of the second chassis conveyor 310 is positioned to engage the outer surfaces of the rollers 315a, 315b, 315d, 315e, 315f. It is to be appreciated that the second chassis conveyor 310 can be arranged and configured other ways than shown in FIGS. 5-9. For example, the second chassis conveyor 310 can include more than one belt and may include different numbers of rollers arranged in different ways.

The following description of the operation of the apparatus 300 is made with reference to FIGS. 1-9. In an upstream manufacturing process, first end regions 172 of first and second side panels 112, 114 are connected with the first waist region 116 of the chassis 102. It is to be appreciated that in different embodiments, the first end regions 172 of the side panels 112, 114 may be connected with either the inner, body facing surface 132 or the outer, garment facing surface 134 of the chassis 102 in the first waist region 116. In addition, as discussed above, the first end regions 172 of the side panels 112, 114 may be connected with the chassis 102 in various ways, such as refastenably and/or permanently. The chassis 102 and side panels 112, 114 may be transferred to the apparatus 300 proximate the roller 314d. As shown in FIGS. 5-7, the outer, garment facing surface 134 of the chassis 102 is positioned in contact with the first surface 316 of the belt 312 of the first chassis conveyor 308. Portions of the chassis 102 extending along the first and second side edges 128, 130 are positioned in contact with the first surfaces 316 of the belts 312 of the first and second panel conveyors 304, 306, respectively. The first and second side panels 112, 114 extend outwardly in the cross direction CD from the first waist region 116 of the chassis 102. As such, the second surface 162 of the first side panel 112 is in contact with the first surface 316 of the belt 312 of the first panel conveyor 304, and the second surface 162 of the second side panel 114 is in contact with the first surface 316 of the belt 312 of the second panel conveyor 306. The first chassis conveyor 308 and the panel conveyors 304, 306 convey the chassis 102 and side panels 112, 114 in a laid out, flat configuration such as shown in FIG. 2 in the first machine direction MD1 until the second waist region 118 advances past the nip 302.

Figure 8:
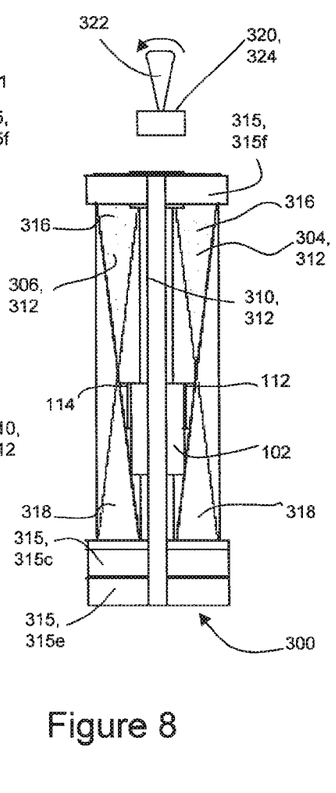
FIG. 8 is a front side view of the converting apparatus of FIG. 6.
Figure 9:
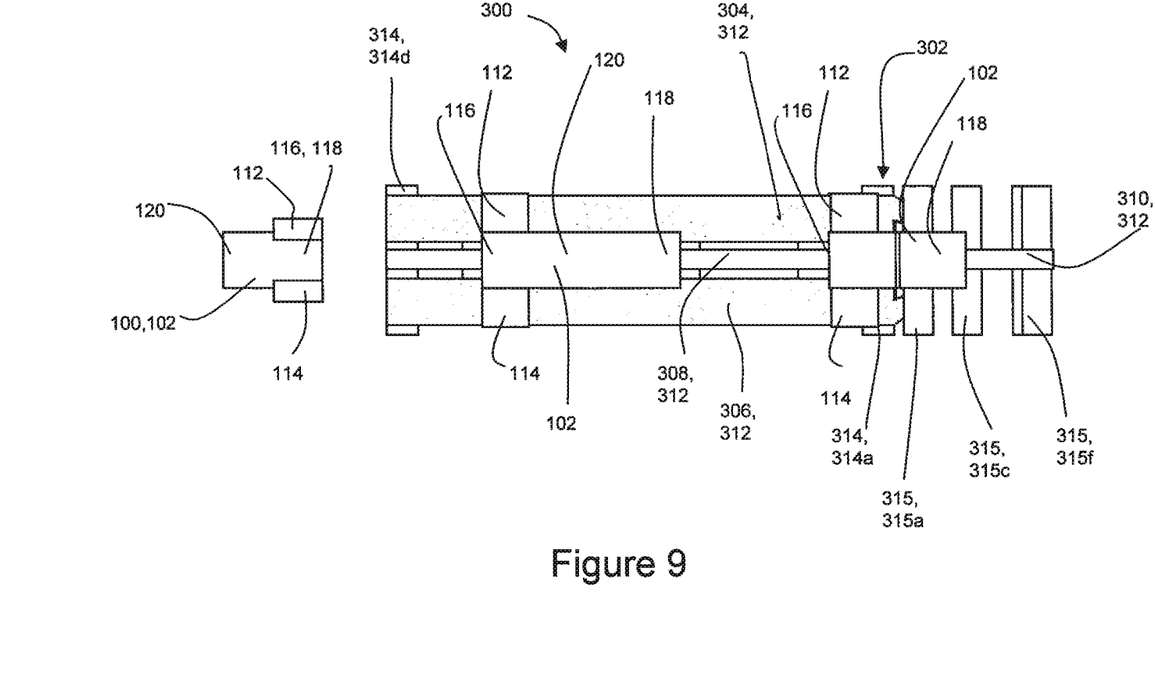
FIG. 9 is a top side view of the converting apparatus of FIG. 6.

Once the second waist region 118 of the chassis 102 advances past the nip 302, a tucking mechanism 320 may redirect the crotch region 120 of the chassis 102 into the nip 302. As the crotch region 120 is redirected into the nip 302, the chassis 102 is folded about a lateral axis 126 wherein the inner, body facing surfaces of the first waist region 116 and the second waist region 118 are brought into a facing relationship. The tucking mechanism 320 is schematically represented in FIGS. 7 and 8. It is to be appreciated that various configurations of tucking mechanisms may be used. For example, tucking mechanism 320 may include one or more blades 322 rotated by a motor 324, wherein the rotating blade(s) is positioned to contact the inner, body facing surface 132 of the chassis 102 in the crotch region 120, thus redirecting the chassis 102 into the nip 302. Various examples of tucking mechanism configurations are disclosed in U.S. Pat. Nos. 4,519,596; 4,650,173; 6,708,855; and 7,617,656, which are hereby incorporated herein by reference.

From the first rollers 314a, 315a, the folded chassis 102 begins to travel in the second machine direction MD2 in a folded configuration such as shown in FIG. 3. As such, the outer, garment facing surface 134 of the first waist region 116 is in contact with the first surface 316 of the belt 312 of the first chassis conveyor 306, and the outer, garment facing surface 134 of the second waist region 118 is in contact with the first surface 316 of the belt 312 of the second chassis conveyor 310. In addition, portions of the chassis 102 extending along the first and second side edges 128, 130 from the crotch region 120 to the first waist region 116 are positioned in contact with the first surfaces 316 of the belts 312 of the first and second panel conveyors 304, 306, respectively. The first and second side panels 112, 114 continue to extend outwardly in the cross direction CD from the first waist region 116 of the chassis 102. As such, the second surface 162 of the first side panel 112 is in contact with the first surface 316 of the belt 312 of the first panel conveyor 304, and the second surface 162 of the second side panel 114 is in contact with the first surface 316 of the belt 312 of the second panel conveyor 306.

As the chassis 102 and the side panels 112, 114 advance in the second machine direction, MD2, the chassis 102 is maintained in a folded configuration by the distance between the belts 312 of the first and second chassis conveyors 308, 310. And the panel conveyors 304, 306 fold the first and second side panels 112, 114. As previously mentioned, the belts 312 of the first and second panel conveyors 304, 306 are twisted 180° in the first twist direction between the first roller 314a and the second roller 314b. Thus, as the chassis 102 and side panels 112, 114 travel in the second machine direction MD2, the first surfaces 316 of the belts 312 the first and second panel conveyors 304, 306 twist and fold the side panels 112, 114 around the central regions 176 to position the second end regions 174 of the side panels 112, 114 in contact with and to connect with the outer, garment facing surface 134 of the second waist region 118 of the chassis 102. As discussed above, the second end regions 174 of the side panels 112, 114 may be connected with the chassis 102 in various ways, such as refastenably and/or permanently. Thus, as the chassis 102 and side panels 112, 114 are placed in a folded configuration such as shown in FIG. 4 before advancing to the second roller 314b.

After the side panels 112, 114 are folded and before advancing to the second roller 314b, the outer, garment facing surface 134 of the first waist region 116 is in contact with the first surface 316 of the belt 312 of the first chassis conveyor 306, and the outer, garment facing surface 134 of the second waist region 118 is in contact with the first surface 316 of the belt 312 of the second chassis conveyor 310. In addition, portions of the chassis 102 extending along the first and second side edges 128, 130 from the crotch region 120 to the second waist region 118 are positioned in contact with the first surfaces 316 of the belts 312 of the first and second panel conveyors 304, 306, respectively. Further, the second surface 162 of the first side panel 112 between the central region 176 and the second end region 174 is in contact with the first surface 316 of the belt 312 of the first panel conveyor 304, and the second surface 162 of the second side panel 114 between the central region 176 and the second end region 174 is in contact with the first surface 316 of the belt 312 of the second panel conveyor 306. Thus, the end regions 172, 174 of the first side panel 112 and the portions of the chassis 102 extending along the first side edge 128 from the crotch region 120 to the waist regions 116, 118 are advanced between the first surface 316 of the first panel conveyor 304 and outer surface of the second roller 314b. Similarly, the end regions 172, 174 of the second side panel 112 and the portions of the chassis 102 extending along the second side edge 130 from the crotch region 120 to the waist regions 116, 118 are advanced between the first surface 316 of the second panel conveyor 304 and outer surface of the second roller 314b. As such, the connections between the side panels 112, 114 and the chassis 102 are compressed between the second roller 314b and the belts 312 of the panel conveyors 304, 306. Such compression may help to secure the connections between the side panels 112, 114 and the chassis 102.

From the second roller 314b, the folded chassis 102 and side panels 112, 114 travel in the third machine direction MD3 and are discharged from the apparatus 300. As previously mentioned, the belts 312 of the first and second panel conveyors 304, 306 are twisted 180° in a second direction (opposite the first twist direction) between the second roller 314b and the third roller 314c to remove the twists from the belts 312.

Figure 10:
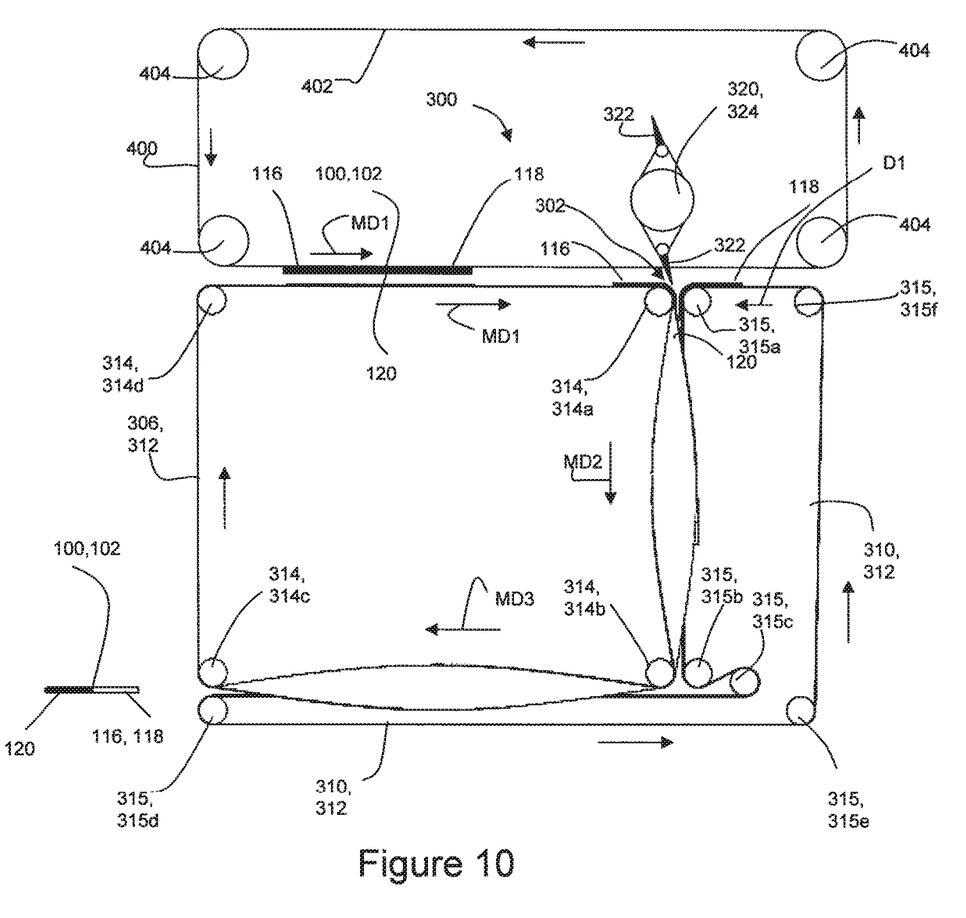
FIG. 10 is a left side view of a second embodiment of the converting apparatus.

It is to be appreciated converting apparatus 300 may be configured in various ways to accommodate a transport the chassis to the nip 302 in various ways. For example, FIG. 10 shows an arrangement wherein the converting apparatus 300 includes a carrier 400 that conveys the chassis 102 and side panels 112, 114 in a laid out, flat configuration such as shown in FIG. 2 in the first machine direction MD1 until the second waist region 118 advances past the nip 302. Once the second waist region 118 of the chassis 102 advances past the nip 302, the chassis 102 and side panels 112, 114 are transferred from the carrier 400 to the first panel conveyor 304, second panel conveyor 306, first chassis conveyor 308, and a second chassis conveyor 310. In particular, the first waist region 116 of the chassis 102 is transferred from the carrier 400 to the first chassis conveyer 304; the side panels 112, 114 are transferred from the carrier 400 to the first and second side conveyors 306, 308; and the second waist region 118 of the chassis 102 is transferred to from the carrier 400 to the second chassis conveyor 310. And a tucking mechanism 320 may redirect the crotch region 120 of the chassis 102 into the nip 302.

The carrier 400 is schematically represented in FIG. 10 in the form of a belt 402 wrapped around four rollers 404. The chassis 102 and side panels 112, 114 may be held on the belt 402 with vacuum before being transferred to the first panel conveyor 304, second panel conveyor 306, first chassis conveyor 308, and second chassis conveyor 310 adjacent the nip 302 as discussed above. Although a single belt is shown in FIG. 10, it is to be appreciated that in some embodiments, the carrier 400 includes more than one belt. It should also be appreciated that in some embodiments the carrier 400 may be configured as a rotating drum. In such an embodiment, the chassis 102 and side panels 112, 114 may be held to the outer surface of the drum with vacuum before being transferred to the first panel conveyor 304, second panel conveyor 306, first chassis conveyor 308, and second chassis conveyor 310 adjacent the nip 302 as discussed above.

The tucking mechanism 320 is schematically represented in FIG. 10. It is to be appreciated that various configurations of tucking mechanisms may be used. For example, tucking mechanism 320 may include one or more blades 322 rotated by a motor 324, wherein the rotating blade(s) is positioned to contact the inner, body facing surface 132 of the chassis 102 in the crotch region 120, thus redirecting the chassis 102 into the nip 302. Various examples of tucking mechanism configurations are disclosed in U.S. Pat. Nos. 4,519,596; 4,650,173; 6,708,855; and 7,617,656, which are hereby incorporated herein by reference. In some embodiments, the tucking mechanism 320 contacts and pushes the inner, body facing surface 132 of the chassis 102 in the crotch region 120 through a hole in the belt 402 to redirect the chassis 102 into the nip 302. In carrier embodiments configured as a drum, the tucking mechanism 320 may contact and push the inner, body facing surface 132 of the chassis 102 in the crotch region 120 through a hole in the outer radial surface of the drum to redirect the chassis 102 into the nip 302.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method for assembling disposable diaper pants, each diaper pant comprising a chassis, a first side panel, and a second side panel, each chassis comprising a topsheet, a backsheet, and an absorbent core disposed between the topsheet and the backsheet, each chassis having a first waist region longitudinally opposed to a second waist region, and a crotch region located between the first and second waist regions, and having a longitudinal axis and a lateral axis, the first and second side panels joining the first waist region and the second waist region to form a waist opening and a pair of leg openings, the method comprising the steps of:
   connecting first end regions of the first and second side panels with the first waist region of the chassis;
   conveying the chassis in a first direction, wherein the backsheet is in direct contact with a moving surface of a first chassis conveyor, and wherein the first and second side panels extend laterally outward from the first waist region with the first side panel positioned on a moving surface of a first panel conveyor and the second side panel positioned on a moving surface of a second panel conveyor;
   advancing the second waist region of the chassis past a nip defined between the first chassis conveyor and a second chassis conveyor;
   folding the chassis to position the second waist region into a facing relationship with the first waist region by redirecting the crotch region of the chassis into the nip;
   conveying the folded chassis in a second direction between the first chassis conveyor and the second chassis conveyor, wherein the first and second side panels extend laterally outward from the first waist region with the first side panel positioned on the moving surface of the first panel conveyor and the second side panel positioned on the moving surface of the second panel conveyor;
   twisting the first and second panel conveyors to position second end regions of the first and second side panels in contact with the second waist region of the chassis;
   connecting the second end regions of the first and second side panels with the second waist region of the chassis.

2. The method of claim 1, further comprising the step of conveying the folded chassis in a third direction from the first roller to a second roller.

3. The method of claim 2, further comprising the step of untwisting the first and second panel conveyors between the first and second rollers.

4. The method of claim 3, wherein the folded chassis advances in the third direction while being held between the first and second chassis conveyors.

5. The method of claim 1, wherein the second end regions of the first and second side panels are permanently connected with the second waist region.

6. The method of claim 1, further comprising the step of compressing the second end regions of the first and second side panels and the second waist region between the moving surface of the first and second panel conveyors and a first roller.

7. The method of claim 1, wherein the second end regions of the first and second side panels are refastenably connected with the second waist region.

8. The method of claim 1, wherein the first end regions of the first and second side panels are permanently connected with the first waist region.

9. The method of claim 1, wherein the first end regions of the first and second side panels are refastenably connected with the first waist region.

10. The method of claim 1, comprising applying vacuum forces to the first and second side panels to hold the first and second side panels in contact with the first and second panel conveyors.

11. The method of claim 10, wherein the vacuum forces are applied only to the second end regions of the first and second side panels.

12. A method for assembling disposable diaper pants, each diaper pant comprising a chassis, a first side panel, and a second side panel, each chassis comprising a topsheet, a backsheet, and an absorbent core disposed between the topsheet and the backsheet, each chassis having a first waist region longitudinally opposed to a second waist region, and a crotch region located between the first and second waist regions, and having a longitudinal axis and a lateral axis, the first and second side panels joining the first waist region and the second waist region to form a waist opening and a pair of leg openings, the method comprising the steps of:
   connecting first end regions of the first and second side panels with the first waist region of the chassis;
   conveying the chassis, first side panel, and second side panel in a first direction on a carrier;
   advancing the second waist region of the chassis past a nip defined between a first chassis conveyor and a second chassis conveyor;
   transferring the chassis from: the carrier to the first and second chassis conveyor, the first side panel to a first panel conveyor, and the second side panel to a second panel conveyor, wherein the backsheet is in direct contact with a moving surface of the first chassis conveyor, and wherein the first and second side panels extend laterally outward from the first waist region with the first side panel positioned on a moving surface of the first panel conveyor and the second side panel positioned on a moving surface of the second panel conveyor;

folding the chassis to position the second waist region into a facing relationship with the first waist region by redirecting the crotch region of the chassis into the nip;

conveying the folded chassis in a second direction between the first chassis conveyor and the second chassis conveyor, wherein the first and second side panels extend laterally outward from the first waist region with the first side panel positioned on the moving surface of the first panel conveyor and the second side panel positioned on the moving surface of the second panel conveyor;

twisting the first and second panel conveyors to position second end regions of the first and second side panels in contact with the second waist region of the chassis;

connecting the second end regions of the first and second side panels with the second waist region of the chassis.

13. The method of claim 12, further comprising the step of compressing the second end regions of the first and second side panels and the second waist region between the moving surface of the first and second panel conveyors and a first roller.

14. The method of claim 12, wherein the carrier comprises a belt.

15. The method of claim 12, further comprising the step of conveying the folded chassis in a third direction from the first roller to a second roller.

16. The method of claim 15, further comprising the step of untwisting the first and second panel conveyors between the first and second rollers.

17. The method of claim 12, wherein the second end regions of the first and second side panels are permanently connected with the second waist region.

18. The method of claim 12, wherein the second end regions of the first and second side panels are refastenably connected with the second waist region.

19. The method of claim 12, wherein the first end regions of the first and second side panels are permanently connected with the first waist region.

20. The method of claim 12, wherein the first end regions of the first and second side panels are refastenably connected with the first waist region.

* * * * *